United States Patent
Prom

(10) Patent No.: US 10,028,746 B2
(45) Date of Patent: Jul. 24, 2018

(54) MEDICAL DEVICE FOR TREATING A TARGET SITE

(71) Applicant: AGA Medical Corporation, Plymouth, MN (US)

(72) Inventor: Darren Todd Prom, Coon Rapids, MN (US)

(73) Assignee: ST. JUDE MEDICAL, CARDIOLOGY DIVISION, INC., St. Paul, MN (US)

( * ) Notice: Subject to any disclaimer, the term of this patent is extended or adjusted under 35 U.S.C. 154(b) by 538 days.

(21) Appl. No.: 13/791,118

(22) Filed: Mar. 8, 2013

(65) Prior Publication Data
US 2014/0257373 A1 Sep. 11, 2014

(51) Int. Cl.
*A61B 17/08* (2006.01)
*A61B 17/12* (2006.01)
*A61B 17/00* (2006.01)

(52) U.S. Cl.
CPC .. *A61B 17/12022* (2013.01); *A61B 17/12031* (2013.01); *A61B 17/12109* (2013.01); *A61B 17/12172* (2013.01); *A61B 2017/00579* (2013.01); *A61B 2017/12054* (2013.01); *A61B 2017/12095* (2013.01)

(58) Field of Classification Search
CPC ........ A61B 17/12022; A61B 17/12031; A61B 17/12172; A61B 17/12109; A61B 2017/12095; A61B 2017/12054; A61B 2017/00579
USPC .......................... 606/213–215, 191, 200, 127
See application file for complete search history.

(56) References Cited

U.S. PATENT DOCUMENTS

| 5,725,552 A | 3/1998 | Kotula et al. | |
|---|---|---|---|
| 6,364,895 B1 * | 4/2002 | Greenhalgh | 606/200 |
| 6,371,971 B1 * | 4/2002 | Tsugita et al. | 606/200 |

(Continued)

OTHER PUBLICATIONS

"AMPLATZER™ Multi-Fenestrated Septal Occluder—'Cribriform';" St. Jude Medical; retrieved on Sep. 18, 2012 from <http://www.sjmprofessional.com/Products/US/structural-heart-therapy/amplatzer-cribriform-occluder.aspx>.

(Continued)

*Primary Examiner* — Diane Yabut
*Assistant Examiner* — Erich Herbermann
(74) *Attorney, Agent, or Firm* — Armstrong Teasdale LLP

(57) ABSTRACT

Embodiments of the present disclosure are directed to medical devices, methods, and systems for delivering a medical device to a target site. In one embodiment, a medical device includes a tubular member having a proximal end and a distal end, the tubular member having an expanded configuration and a relaxed configuration. The medical device further includes a tether comprising a first end and a second end, the first end coupled to the proximal end or the distal end of the tubular member. In addition, the medical device includes an engagement member coupled to the second end of the tether and disposed at least partially within the tubular member and between the proximal and distal ends of the tubular member in the relaxed configuration. The engagement member is configured to engage the proximal or distal end of the tubular member, opposite the first end of the tether, upon displacement of the proximal and distal ends of the tubular member towards one another, such that the tubular member is locked in the expanded configuration.

23 Claims, 7 Drawing Sheets

(56) References Cited

U.S. PATENT DOCUMENTS

| | | | |
|---|---|---|---|
| 7,442,200 B2 * | 10/2008 | Mazzocchi et al. | 606/200 |
| 8,034,061 B2 * | 10/2011 | Amplatz et al. | 606/151 |
| 8,162,974 B2 | 4/2012 | Eskuri et al. | |
| 2002/0111647 A1 | 8/2002 | Khairkhahan et al. | |
| 2002/0143349 A1 * | 10/2002 | Gifford et al. | 606/157 |
| 2005/0273135 A1 * | 12/2005 | Chanduszko et al. | 606/213 |
| 2005/0288786 A1 | 12/2005 | Chanduszko | |
| 2007/0276415 A1 | 11/2007 | Kladakis | |
| 2009/0099647 A1 | 4/2009 | Glimsdale et al. | |
| 2009/0281567 A1 | 11/2009 | Osypka | |
| 2010/0222810 A1 | 9/2010 | Debeer et al. | |
| 2011/0082495 A1 | 4/2011 | Ruiz | |
| 2011/0184452 A1 * | 7/2011 | Huynh et al. | 606/195 |
| 2012/0065667 A1 | 3/2012 | Javois et al. | |
| 2012/0172973 A1 * | 7/2012 | Deckard et al. | 623/1.16 |

OTHER PUBLICATIONS

Freed, B. H., et al.; "*Percutaneous Transcatheter Closure of the Native Aortic Value to Treat De Novo Aortic Insufficiency After Implantation of a Left Ventricular Assist Device*;" JACC: Cardiovascular Interventions; vol. 5, No. 3; dated 2012.

\* cited by examiner

MEDICAL DEVICE FOR TREATING A TARGET SITE

BACKGROUND

I. Field of the Disclosure

The present disclosure relates generally to medical devices for treating target sites. More particularly, the present disclosure is directed to devices and methods for treating areas within a patient's body, such as an aortic valve.

II. Description of the Related Art

A wide variety of intravascular devices are used in various medical procedures. Certain intravascular devices, such as delivery devices and guidewires, are generally used to deliver fluids or other medical devices to specific locations within a patient's body, such as a select site within the vascular system. Other, frequently more complex medical devices are used to treat specific conditions, such as medical devices used to occlude a target site.

BRIEF SUMMARY

Embodiments of the present disclosure are directed to medical devices, systems, and methods for treating a target site. In one embodiment, a medical device for treating a target site is provided. The medical device comprises a tubular member having a proximal end and a distal end. The tubular member has an expanded configuration and a relaxed configuration, wherein the relaxed configuration comprises at least one disk member. The tubular member is configured to be constrained from the relaxed configuration to a reduced configuration for delivery to the target site, and the tubular member is further configured to at least partially return from the reduced configuration to the relaxed configuration when unconstrained. The medical device also includes a tether comprising a first end and a second end, wherein the first end is coupled to the proximal end or the distal end of the tubular member. Moreover, the medical device includes an engagement member coupled to the second end of the tether and disposed at least partially within the tubular member and between the proximal and distal ends of the tubular member in the relaxed configuration. The engagement member is configured to engage the proximal or distal end of the tubular member, opposite the first end of the tether, upon displacement of the proximal and distal ends of the tubular member towards one another such that the tubular member is locked in the expanded configuration.

According to another embodiment, a medical device for treating a target site comprises a tubular member having a proximal end and a distal end, wherein the tubular member has an expanded configuration and is configured to be constrained to a reduced configuration for delivery to the target site. The medical device further includes a tether comprising a first fixed end and a second free end, wherein the first fixed end is coupled to the distal end of the tubular member. The medical device also includes an engagement member coupled to the second free end of the tether and configured to engage the proximal or distal end of the tubular member, opposite the first fixed end of the tether, such that the tubular member is locked in the expanded configuration. In addition, the medical device includes a holder disposed on the tether and between the first fixed end and the second free end thereof, wherein the holder is configured to house the engagement member therein when the tubular member is in the reduced configuration. The engagement member is configured to be displaced from the holder to engage the proximal end or the distal end of the tubular member, opposite the first fixed end of the tether, in the expanded configuration.

In one embodiment, a method of delivering a medical device is provided. The method comprises providing a medical device comprising an expanded configuration and a relaxed configuration and attaching the medical device to a delivery device. The medical device also includes advancing the delivery device and the medical device in a reduced configuration to the target site and deploying the medical device at the target site. Deploying the medical device comprises displacing the medical device relative to the delivery device to expand the medical device from the relaxed configuration to the expanded configuration and to engage a proximal end or a distal end of the medical device with an engagement member such that the medical device is locked in the expanded configuration. The method further includes detaching the medical device from the delivery device.

According to another embodiment, a system for delivering a medical device to a target site is provided. The system includes a medical device comprising an expanded configuration, a relaxed configuration, and an engagement member. The system also includes a delivery device comprising a coupling member configured to removably attach to the engagement member at a proximal end or a distal end of the medical device. The medical device is configured to be displaced relative to the delivery device such that the medical device expands from the relaxed configuration to the expanded configuration, wherein expansion of the medical device is configured to facilitate engagement of the engagement member such that the medical device is locked in the expanded configuration

BRIEF DESCRIPTION OF THE DRAWINGS

The foregoing features and advantages of embodiments in accordance with the present disclosure will become apparent to those skilled in the art from the following detailed description, especially when considered in conjunction with the accompanying drawings in which like numerals in the several views refer to corresponding parts.

DETAILED DESCRIPTION

Figure 1:
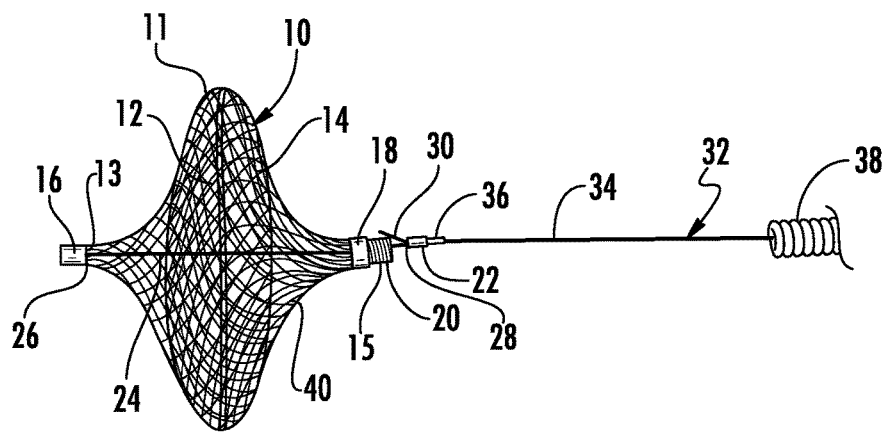
FIG. 1 is a schematic illustration of a medical device in an expanded configuration and a delivery device according to an embodiment of the present disclosure.

Several factors affect the effectiveness of the medical device to treat the target site, such as the flexibility of the medical device. For example, medical devices having more flexibility provide the ability to conform to a variety of target sites and to be delivered through tortuous pathways. More flexible medical devices, such as occlusion devices, may also be capable of being formed of more flexible materials for improving thrombogenicity. However, more flexible devices may exhibit less retention force thereby allowing the device to migrate from the target site. In addition, although less flexible devices may add additional retention force, these devices risk injuring the target site due to excessive retention force. Other factors affect the ability of the medical device to be delivered to the target site, such as the size of the medical device for delivery within a delivery device.

Therefore, it would be advantageous to provide a medical device which offers improved flexibility, retention, and thrombogenicity for treating a target site, as well as delivery to the target site.

As described in greater detail below, medical devices in accordance with the present disclosure are configured to treat a target site. In one embodiment, the medical device is configured to be locked in an expanded configuration. Thus, the medical device may be formed of more flexible materials and be configured to be constrained to a smaller reduced diameter than conventional devices. In addition, by being locked in an expanded position, the medical device facilitates improved retention at the target site to reduce the incidence of migration.

It is understood that the use of the term "target site" is not meant to be limiting, as the medical device may be configured to treat any target site within a patient's body, such as an abnormality, a vessel, an organ, an opening, a chamber, a channel, a tunnel, a hole, a cavity, a body lumen, a valve, or the like, located anywhere in the body. The medical device may be suitable for selective occlusion of a target site anywhere in the body's circulatory system where it is desired to reduce or stop the flow of blood. The medical device may also be deployed in a variety of manners with respect to a target site, such a proximate or adjacent to the target site, at the target site, or within the target site. Moreover, although examples are provided of a medical device that is used for treating a target site within the circulatory system, such as for the closure of an aortic valve, it is understood that embodiments of the medical device may be used for various applications. In addition, although the medical device is herein described in connection with a delivery device, it is further understood that the medical device may be used with other catheters, delivery sheathes, device loaders, and other accessories. As also used herein, the term "proximal" refers to a portion of the referenced component of a medical device that is closest to the operator, and the term "distal" refers to a portion that is farthest away from the operator at any given time as the medical device is delivered to the target site.

Embodiments of the present disclosure are described more fully hereinafter with reference to the accompanying drawings, in which some, but not all, embodiments are shown. Indeed, the disclosure may be embodied in many different forms and should not be construed as limited to the embodiments set forth herein; rather, these embodiments are provided so that this disclosure will satisfy applicable legal requirements. Like numbers refer to like elements throughout.

Turning now to the specific embodiments set forth in the accompanying drawings. FIG. 1 depicts one embodiment of medical device 10, which is configured to treat a target site, such as a target site in a patient's body. Embodiments of medical device 10 generally comprise tubular member 11, distal disk 12, distal end 13, proximal disk 14, proximal end 15, distal clamp 16, and proximal clamp 18. As depicted, tubular member 11 has two enlarged lobe members, proximal disk 14 and distal disk 12, although more or less lobes are possible. Proximal end 15 of tubular member 11 is secured by proximal clamp 18, while distal end 13 of tubular member 11 is secured by distal clamp 16. Proximal clamp 18 may also be coupled to threaded proximal coupling 20, wherein threaded proximal coupling 20 is configured to engage engagement member 22, as further detailed below.

FIG. 1 further illustrates that medical device 10 includes tether 24 comprising first fixed end 26 and second free end 28. First fixed end 26 is coupled to distal end 13 of tubular member 11. Second free end 28 is coupled to proximal end 15 in an expanded (e.g., locked and deployed) configuration shown in FIG. 1. In this regard, second free end 28 of tether 24 comprises engagement member 22 that is configured to engage proximal end 15 such that tubular member 11 is locked in the expanded configuration. In particular, FIG. 1 shows that a distal end of engagement member 22 includes at least one spoke 30 configured to engage threaded proximal coupling 20 at proximal end 15 of tubular member 11 in the expanded configuration. Delivery device 32 comprising inner wire 34 with coupling member 36 is configured to engage a proximal end of engagement member 22 for displacing proximal 15 and distal 13 ends of tubular member 11 with respect to one another. In this regard, inner wire 34 is configured to displace proximal 15 and distal 13 ends towards one another when coupling member 36 is engaged with engagement member 22 such that spoke 30 is positioned proximally of proximal end 15 to thereby engage threaded proximal coupling 22. Delivery device 32 also includes outer wire 38 that is configured to engage threaded proximal coupling 20 for recapturing medical device 10 prior to tubular member 11 being locked in the expanded configuration, as explained in further detail below.

Figure 2:
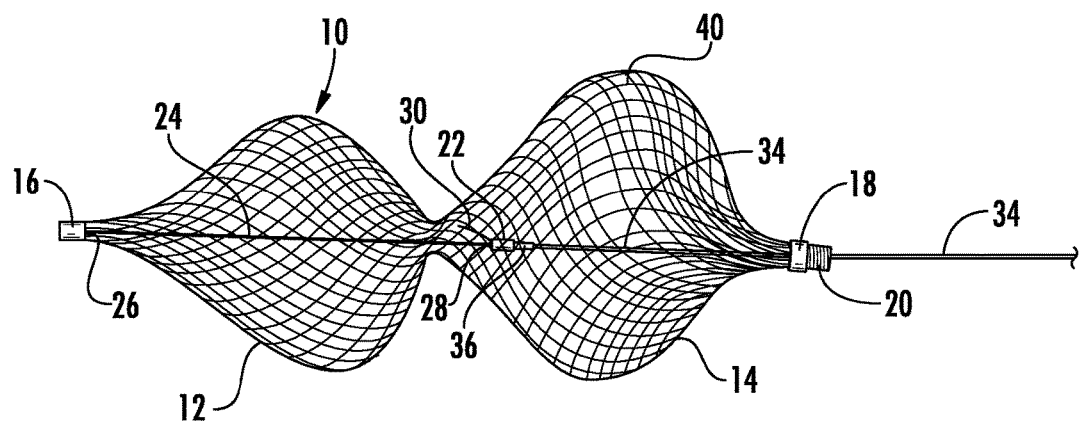
FIG. 2 is a schematic illustration of the medical device of FIG. 1 in a relaxed configuration.

FIG. 1 shows distal disk 12 and proximal disk 14 in an expanded, locked configuration, while FIG. 2 shows disks 12, 14 in a relaxed, partially deployed state. Disks 12, 14 are shown as having a convex outer surface in the relaxed configuration and are configured to obtain a generally conical shape in the expanded, locked configuration. When disks 12, 14 are positioned adjacent to one another, disks 12, 14 may be generally geometrically symmetric, although disks may be asymmetric depending on the target site being treated. In one embodiment, disks 12, 14 may be configured for placement at an aortic valve such that each disk 12, 14 is disposed on opposite sides of, and overlies the opening of, the valve. Thus, disks 12, 14 may be biased towards one another in the expanded configuration such that disks 12, 14 are "clamped" into position on either side of the valve when locked in the expanded configuration (shown in FIG. 8).

As used herein, the term "disk" is not meant to be limiting and may be a member having a circular, an oval, a conical, a frustoconical, a discoid, or other shape having a cross-sectional dimension configured to overlie or engage a target site, such as for substantially precluding or impeding flow through an opening at the target site. Although FIG. 1 illustrates tubular member 11 with proximal disk 14 and distal disk 12, it is understood that tubular member 11 may have one or more disks 12, 14 depending on the target site and particular application. Tubular member 11 may have a preset configuration and be configured to be constrained to a reduced configuration for delivery to a target site and at least partially return to its preset configuration. For example, tubular member 11 may be heat set in a particular configuration and if formed of a shape-memory material, may be constrained to a reduced configuration (e.g., by axial elongation) and biased such that tubular member 11 is configured to self expand from the reduced configuration and return towards the preset configuration. FIG. 2 illustrates one embodiment with tubular member 11 in a relaxed state or configuration, which may correspond to tubular member 11 in a preset configuration. Thus, when tubular member is compressed from the relaxed state (FIG. 2) towards the expanded configuration (FIG. 1), a maximum outer diameter of tubular member 11 (e.g., distal 12 and proximal 14 disk members) will expand further than in the relaxed state. In addition, because tubular member 11 is naturally biased towards the preset configuration when relaxed, proximal end 15 of tubular member 11 will be locked in position due to engagement of spoke 30 with threaded proximal coupling 20 when in the expanded configuration.

Figure 4:
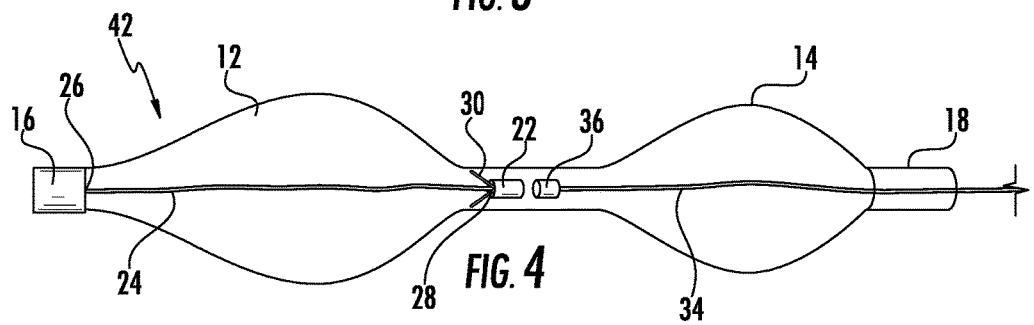
FIG. 4 is a schematic illustration of the medical device from FIG. 3 in a reduced configuration.
Figure 4A:
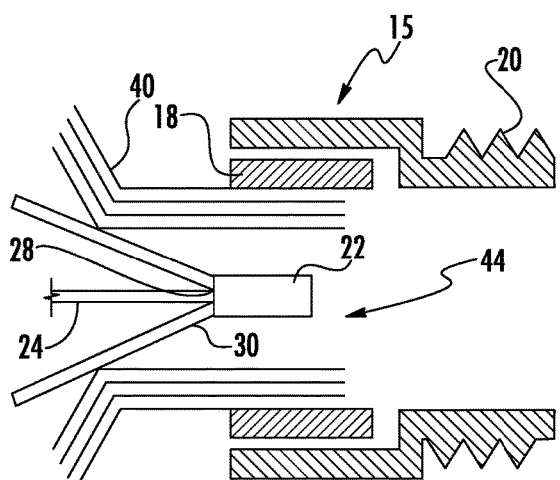
FIG. 4A is an enlarged cross-sectional view of a proximal end of the medical device from FIG. 3.

Tubular member 11 may be formed of a braided fabric comprising a plurality of braided strands 40 (see e.g., FIGS. 1, 2, and 4A). Although the term "tubular" is used, it is understood that tubular member 11 may be braided into a continuous tubular body (having one or more or two ends), comprise a sheet of material that is formed into a tubular shape, or be otherwise formed. In addition, tubular member 11 may comprise one or more layers of braided fabric. According to one embodiment of the present disclosure, tubular member 11 includes a braided fabric formed of a plurality of strands 40, wherein each of strands 40 has a predetermined relative orientation with respect to one another (e.g., a helical braid). Moreover, medical device 10 may comprise a plurality of layers of braided or other occluding material such that the device is capable of at least partially inhibiting blood flow therethrough in order to facilitate the formation of thrombus and epithelialization around medical device 10. Although the term "strand" is discussed herein, "strand" is not meant to be limiting, as it is understood tubular member 11 may comprise one or more wires, cords, fibers, yarns, filaments, cables, threads, or the like, such that these terms may be used interchangeably. Strands 40 may be braided, interwoven, or otherwise combined to define generally tubular member 11. One may solder, braze, weld, coat, glue, clamp, tie or otherwise affix the ends of braided strands 40 together, such as with marker bands or clamps 16, 18 shown in FIGS. 1, 2, and 4A. Thus, although the term "clamp" is used herein, any securement technique or mechanism may be used to secure the ends of strands 40 together to prevent unraveling. Some braiding techniques (e.g., formation of a tubular braid having one closed end and open end) or sufficient heat setting of tubular member 11 may render one or both clamps 16, 18 unnecessary. According to one embodiment, strands 40 at proximal end 15 may be affixed to an external surface of threaded proximal coupling 20, such as with swaging or welding of proximal clamp 18 whereby strands 40 are secured between proximal clamp 18 and threaded proximal coupling 20. However, FIG. 4A illustrates an alternative embodiment where strands 40 may be secured internally within proximal clamp 18. In either case, a through lumen may be provided in proximal end 15 that is configured to receive tether 24, as depicted in FIG. 4A.

Strands 40 of a metal fabric used in one embodiment may be formed of a material that is both resilient and that can be heat treated to substantially set a desired preset shape. One class of materials which meets these qualifications is shape memory alloys. One example of a shape memory alloy is Nitinol. It is also understood that medical device 10 may comprise various materials other than Nitinol that have elastic and/or memory properties, such as spring stainless steel, trade named alloys such as Elgiloy®, Hastelloy®, CoCrNi alloys (e.g., trade name Phynox), MP35N®, CoCrMo alloys, or a mixture of metal and polymer fibers. Depending on the individual material selected, strand 40 diameter, number of strands 40, and pitch may be altered to achieve the desired properties of medical device 10.

FIGS. 1 and 2 illustrate one embodiment of tether 24 having fixed end 26 and opposite free end 28. Tether 24 may comprise a flexible material and in some embodiments, tether 24 may, for example, be a solid wire and may comprise Nitinol or other super elastic or metal alloy material (e.g., stainless steel). However, in other cases, tether 24 could be one or more wires, cords, fibers, yarns, filaments, cables, threads, or the like. Fixed end 26 of tether 24 is secured to distal end 13 of tubular member 11, such as via clamp 16, a marker band, welding, or other securement feature. As shown in FIG. 1, tether 24 has a length that approximates a length between proximal 15 and distal 13 ends of tubular member 11 in the expanded, locked configuration. FIG. 2 shows that tether 24 has a length that is less than a length between proximal 15 and distal 13 ends of tubular member 11 in a relaxed configuration wherein proximal 15 and distal 13 ends are displaced away from one another. In some embodiments, tether 24 may extend axially through an approximate center of tubular member 11.

Tether 24 comprises at least one spoke 30. As shown in FIG. 1, spoke 30 is coupled to, and extends radially outward from, a distal end of engagement member 22. FIG. 2 shows spoke 30 in an unrestrained state within tubular member 11 when tubular member 11 is in a relaxed configuration. Spoke 30 is configured to directly engage proximal end 15, and in particular threaded proximal coupling 20, to lock medical device 10 in the expanded configuration shown in FIG. 1. Thus, each spoke 30 has a length sufficient to extend from engagement member 22 and engage threaded proximal coupling 20 and is of sufficient strength to lock medical device 10 in the expanded configuration without spoke 30 being deformed or otherwise distorted. For example, spoke 30 may be biased into engaging contact with threaded proximal coupling 20. With reference to FIG. 1, in the locked, expanded configuration, spoke 30 engages threaded proximal coupling 20, and due to the disposition of tubular member 11 to be biased towards the relaxed state (FIG. 2), the spoke 30 restrains displacement of proximal 15 and distal 13 ends of tubular member 11 away from one another. In other embodiments, clamp 18 and threaded proximal coupling 20 are coupled to one another or may be an integral component. Spoke 30 may be attached to engagement member 22 using any suitable securement technique, such as swaging or welding. Moreover, tether 24 may include one or more spokes 30, and the term "spoke" is not meant to be limiting, as spoke 30 may be any feature configured to lock tubular member 11 in the expanded configuration.

According to example embodiments, tether 24 comprises any number of spokes 30, such as 1 spoke, 2-3 spokes, 2-4 spokes, 2-5 spokes, 2-6 spokes, 2-7 spokes, 2-8 spokes, 2-9 spokes, or 2-10 spokes. Thus, medical device 10 may include any number of spokes 30 for facilitating engagement with clamp 18 and/or threaded proximal coupling 22. Spoke 30 may be formed from a flexible and shape-memory material (e.g., Nitinol) or may comprise various materials other than Nitinol that have elastic and/or shape memory properties, such as spring stainless steel, Elgiloy®, Hastellow®, CoCrNi alloys (e.g., Phynox®), MP35N®, CoCrMo alloys, and the like, such that spoke 30 is configured to be flexed from an expanded position to a constrained position for displacement through clamp 18 and threaded proximal coupling 20 and is biased to naturally return to the expanded position for engaging threaded proximal coupling 20 when unconstrained. Furthermore, FIGS. 1 and 3-6 show that each spoke 30 may be oriented in an outward, proximal-to-distal direction. Such an orientation of spoke 30 in its expanded position facilitates locking engagement with threaded proximal coupling 20 since spoke 30 resists displacement of proximal 13 and distal 15 ends away one another. In one embodiment, spoke 30 is a single wire strand having a diameter of about 0.003-0.005 inches (0.076-0.127 mm).

Figure 3:
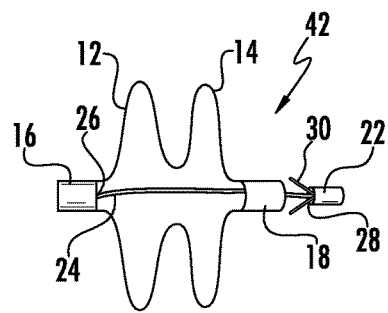
FIG. 3 is a schematic illustration of a medical device in an expanded configuration according to another embodiment of the present disclosure.

FIGS. 3 and 4 illustrate an additional embodiment of medical device 42. Similar to medical device 10, medical device 42 includes distal disk 12, proximal disk 14, distal clamp 16, and proximal clamp 18. As before, medical device 42 may be formed of a braided metal fabric. FIG. 3 illustrates that each of disks 12, 14 is generally disk shaped (i.e., thin, flat, rounded) in an expanded configuration, although as discussed above, disks 12, 14 may have any desired shape. Medical device 42 also includes engagement member 22 and a plurality of spokes 30 coupled to tether 24. Tether 24 may include a first fixed end 26 attached to distal clamp 16 and a second free end 28 attached to engagement member 22. In this embodiment, threaded proximal coupling 20 may be omitted in which case spoke 30 is configured to directly engage proximal clamp 18 with plurality of spokes 30, as shown in FIG. 3. Thus, in some embodiments spoke 30 is configured to be biased into engaging contact with clamp 18 rather than threaded proximal coupling 20 to thereby lock tubular member 11 in the expanded configuration. As shown in FIG. 3, spokes 30 are located just outside proximal clamp 18 and biased radially outward so that tubular member 11 may be locked in the expanded configuration.

FIG. 4 shows medical device 42 in a reduced configuration wherein distal 16 and proximal 18 clamps have been displaced away from one another and thereby constrained to a reduced shape from a relaxed configuration. FIG. 4 also shows that in the reduced configuration, engagement member 22 and spokes 30 are disposed within medical device 42 and that inner wire 34 is configured to engage engagement member 22 with coupling device 36 in the reduced configuration. In particular, FIG. 4 shows coupling member 36 proximate to engagement member 22 and prior to attachment therewith.

Free end 28 of tether 24 is configured to be axially displaceable through opening 44 defined through proximal end 15 of tubular member 11, as shown in FIG. 4A. As illustrated, clamp 18 and threaded proximal coupling 20 may define through opening 44, wherein opening 44 extends axially through clamp 18 and threaded proximal coupling 22. The opening 44 is also defined through the proximal ends of strands 40. As shown, tether 24 and engagement member 22 have a smaller outer diameter than the inner diameter of opening 44 such that tether 24 and engagement member 22 are sized for displacement through opening 44. As such, opening allows tether 24 to be axially displaced as tubular member 11 is moved between a reduced configuration and an expanded, locked configuration.

In addition, engagement member 22 and spokes 30 are configured to be displaced through opening 44, which facilitates engagement of spokes 30 with threaded proximal coupling 20 in the expanded configuration. In particular, FIG. 4A shows that spokes 30 are also sized to be displaced through opening 44. In particular, spokes 30 are shown as being radially expanded and into contact with strands 40. Due to the resilience of spokes 30, spokes 30 are biased towards strands 40, clamp 18, and threaded proximal coupling 20 as spokes 30 are displaced axially through opening 44. Due to the proximal-to-distal orientation of spokes 30, spokes 30 are able to be displaced through opening 44 until fully displaced therefrom. In this regard, spokes 30 are radially constrained until spokes 30 are displaced proximally of clamp 18 and threaded proximal coupling 20, wherein spokes are able to fully radially expand. Once fully expanded, spokes 30 are configured to engage threaded proximal coupling 22 to lock tubular member 11 in the expanded, locked configuration. FIG. 4A further illustrates that threaded proximal coupling 20 may include a threaded outer surface to facilitate engagement with outer delivery wire 38.

Figure 5:
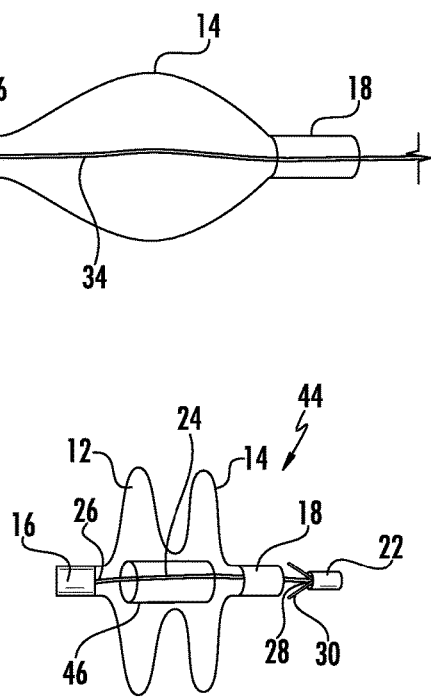
FIG. 5 is a schematic illustration of a medical device in an expanded configuration according to another embodiment of the present disclosure.
Figure 6:
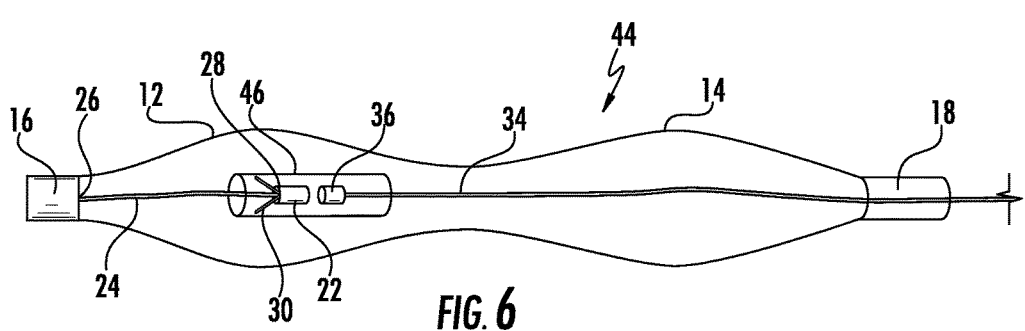
FIG. 6 is a schematic illustration of the medical device from FIG. 5 in a reduced configuration.

In one embodiment, tether 24 has an outer diameter of about 0.003-0.007 inches (0.076-0.178 mm). According to one embodiment, an outer diameter of engagement member 22, inner delivery wire 34, and/or coupling member 36 is about 0.01-0.03 inches (0.25-0.76 mm), while an inner diameter of threaded proximal coupling 20 may be about 0.001-0.005 inches (0.025-0.127 mm) larger than the outer diameter of engagement member 22, inner delivery wire 34, and/or coupling member 36. For example, the inner diameter of threaded proximal coupling 20 may be about 0.025-0.030 inches (0.635-0.762 mm). Sizing the inner diameter of threaded proximal coupling 20 to be larger than the outer diameter of engagement member 22, inner delivery wire 34, and/or coupling member 36 allows engagement member 22, inner delivery wire 34, and/or coupling member 36 to be axially displaced through opening 44 as described above with reference to FIG. 4A FIGS. 5 and 6 illustrate another embodiment of medical device 44. Similar to medical devices 10, 42, medical device 44 includes distal disk 12, proximal disk 14, distal clamp 16, and proximal clamp 18. Medical device 44 also includes tether 24 coupled to engagement member 22. The embodiment shown in FIGS. 5 and 6 illustrate that medical device 44 may further include holder 46. Holder 46 is disposed on tether 24 and between first fixed end 26 and second free end 28 thereof, wherein holder 46 surrounds tether 24. In some instances, tether 24 is coaxial to holder 46. Holder 46 is configured to house engagement member 22 and spoke 30 therein (see FIG. 6). In this regard, holder 46 may surround, and be coaxial to, engagement member 22. In addition, holder 46 may surround spoke 30 to house spoke therein. Thus, holder 46 may be sized to have an inner diameter smaller than a maximum expandable diameter of spoke 30 such that spoke 30 is constrained in a reduced configuration when contained within holder 46. For example, holder 46 may be cylindrical in shape, although other shapes may be used. Engagement member 22 and spoke 30 are configured to be displaced from holder 46 to engage threaded proximal coupling 20 in the expanded, locked configuration (see FIG. 5). In this regard, holder 46 is axially displaceable along tether 24 such that engagement member 22 and spoke 30 may also be axially displaceable with respect to holder 46. Spoke 30 and holder 46 may be capable of moving together in cooperation with one another. For example, spoke 30 and holder 46 may move together proximally at least until holder 46 is adjacent to clamp 18. In this position, holder 46 may engage clamp 18 such that tether 24, engagement member 22, and spoke 30 may be displaced proximally from within holder 46 and through clamp 18 as holder 46 is maintained adjacent to clamp 18 and within tubular member 11.

FIGS. 5 and 6 also illustrate that holder 46 has a shorter length than tether 24. Holder 46 may be used to prevent spoke 30 from engaging tubular member 11 during deployment of medical device 10 (FIG. 6) since spoke 30 is prevented from expanding and engaging tubular member 11 prior to tubular member 11 reaching the expanded, locked configuration (FIG. 5). For example, holder 46 may be sized and configured to abut proximal clamp 18 and/or threaded proximal coupling 20 when moving proximal 14 and distal 12 disks towards one another. In this regard, outer diameter of holder 46 may be larger than inner diameter of clamp 18 such that holder 46 is incapable of being axially displaced through opening 44. Thus, as engagement member 22 and spoke 30 are withdrawn proximally, holder 46 is sized to engage clamp 18 to thereby prevent holder 46 from further axial displacement. As engagement member 22 and spoke 30 are further displaced proximally through opening 44 in clamp 18 and threaded proximal coupling 20 and outward of holder 46, spoke 30 may bias outwardly until fully displaced through the opening to engage threaded proximal coupling 20. Thus, spoke 30 is free to fully radially expand once displaced proximally of threaded proximal coupling 20 wherein spoke 30 is no longer radially constrained.

Figure 7:
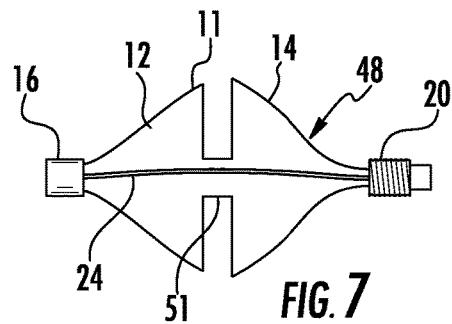
FIG. 7 is a schematic illustration of a medical device in a relaxed configuration according to another embodiment of the present disclosure.
Figure 8:
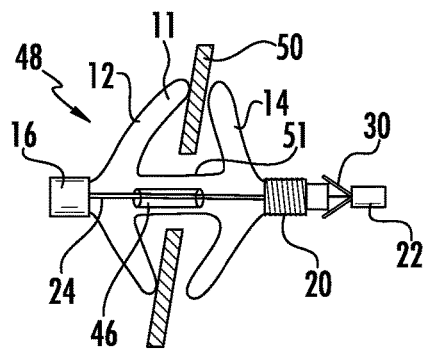
FIG. 8 is a cross-sectional view of the medical device from FIG. 7 in an expanded configuration deployed at a target site.
Figure 9:
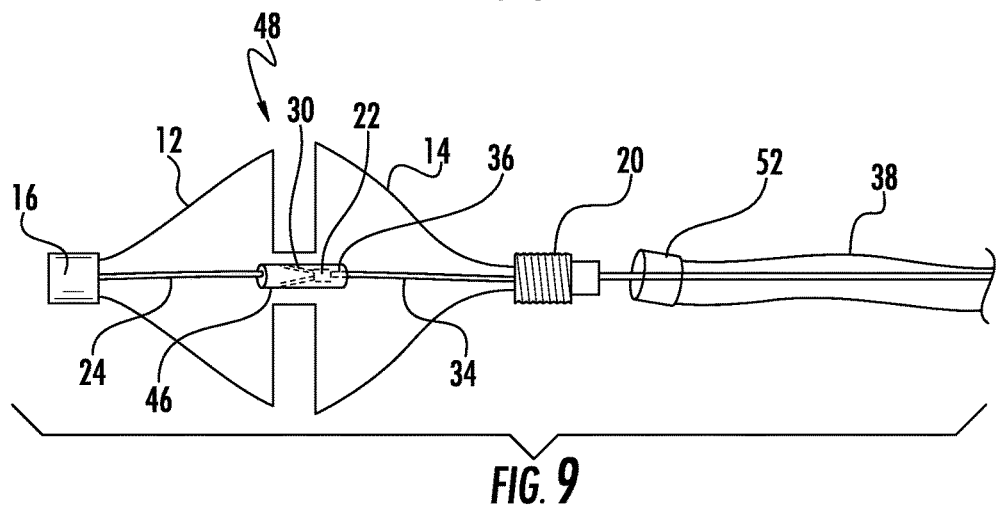
FIG. 9 is a schematic illustration of the medical device from FIG. 7 in a relaxed configuration and a delivery device according to one embodiment of the present disclosure.

FIGS. 7-9 illustrate another embodiment of medical device 48. Similar to medical device 10, 42, 44, medical device 48 includes distal disk 12, proximal disk 14, distal clamp 16, and threaded proximal coupling 20. In this particular embodiment, each of the disks 12, 14 has a conical configuration in relaxed state, which may be a preset configuration as discussed above and shown, for example, in FIG. 1. As also discussed above, tether 24 extends between distal clamp 16 and threaded proximal coupling 20 in an expanded, locked configuration. In this regard, FIG. 8 shows medical device 48 in an expanded, locked configuration wherein proximal disk 14 and distal disk 12 are in engagement on opposite sides of target site 50. As shown, target site 50 defines an opening through which tubular member 11 at least partially extends and proximal disk 14 is located on one side of the opening and distal disk 12 is located on an opposite side of the opening. In this regard, tubular member 11 may define reduced diameter portion 51 that is sized and configured to extend through the opening at target site 50. In the expanded, locked configuration, medical device 48 is configured to provide a clamping force on target site 50, such as thin membrane, due to distal clamp 16 and proximal threaded proximal coupling 20 being displaced towards one another. FIG. 9 illustrates that inner delivery wire 34 may engage engagement member 22 within holder 46, wherein engagement member 22 and spokes 30 are disposed within holder 46, as explained in further detail with reference to FIG. 13. Should medical device 10 need to be recaptured prior to being fully deployed, FIG. 9 shows that outer delivery wire 38 may include coupling member 52 configured to releasably attach to threaded proximal coupling 20, as explained in further detail with reference to FIGS. 11 and 12.

Figure 10:
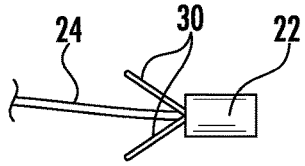
FIG. 10 is an enlarged schematic illustration of an engagement member and a tether according to an embodiment of the present disclosure.
Figure 11:
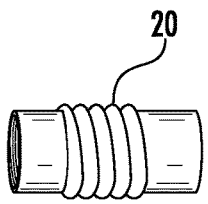
FIG. 11 is an enlarged schematic illustration of a threaded proximal coupling according to an embodiment of the present disclosure.
Figure 12:
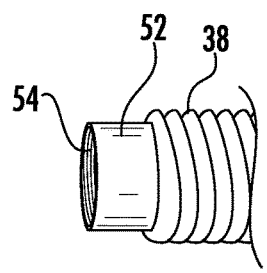
FIG. 12 is an enlarged schematic illustration of a coupling member of a delivery device according to an embodiment of the present disclosure.

FIG. 10 shows an enlarged view of tether 24 coupled to engagement member 22 and spokes 30. As shown, at least a pair of spokes 30 extend outwardly from engagement member 22 and are configured to engage threaded proximal coupling 20 thereby locking tubular member in the expanded configuration (see FIG. 8). FIG. 11 shows one embodiment of threaded proximal coupling 20 having a partially threaded external surface. Thus, in one embodiment, threaded proximal coupling 20 may be configured as an end screw with at least a portion having an externally threaded surface configured to engage with an internally threaded surface. FIG. 12 illustrates that coupling member 52 may include internal threads 54 configured to threadably engage and disengage externally threaded proximal coupling 20 depending on the direction in which outer delivery wire 38 is rotated. In addition, other suitable techniques may be used to engage and disengage coupling member 52 from threaded proximal coupling 20 in response to manipulation of outer delivery wire 38 while providing the ability to transmit torque, such as a press fit, snap fit, twist-fit, and the like. Moreover, the threaded engagement between coupling member 52 and threaded proximal coupling 20 could be reversed if desired such that coupling member 52 is externally threaded and threaded proximal coupling 20 is internally threaded. As also shown in FIG. 12, outer delivery wire 38 may include a wound or coiled wire or outer surface that sufficient rigidity for advancement through a delivery catheter.

Figure 13:
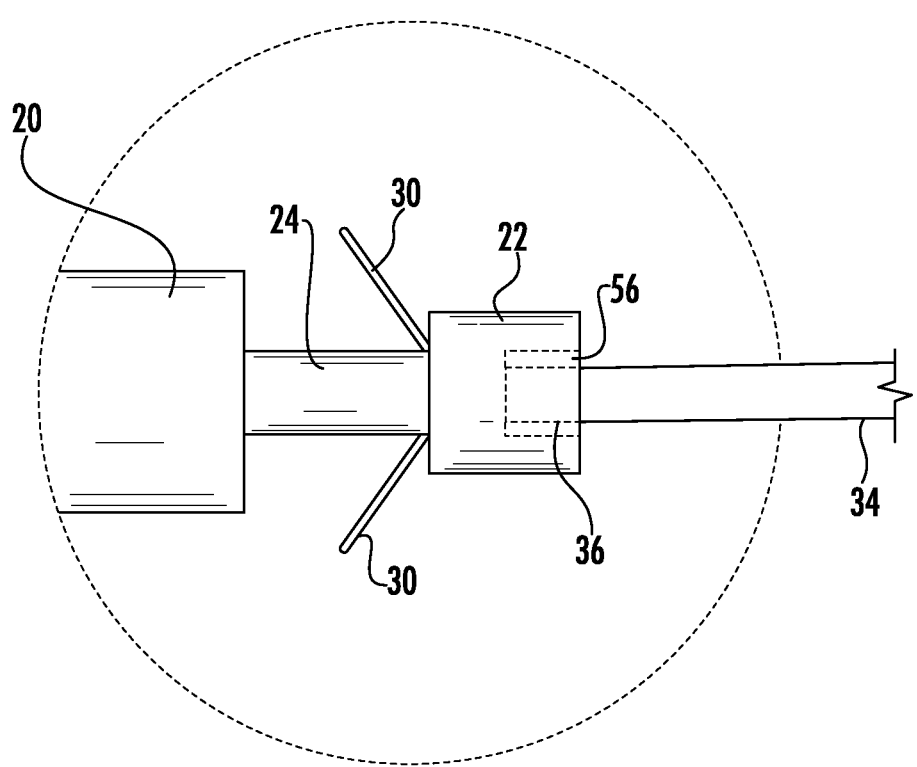
FIG. 13 is an enlarged schematic illustration of a coupling member of a delivery device in engagement with an engagement member of the medical device according to an embodiment of the present disclosure.

FIG. 13 illustrates an enlarged view of threaded proximal coupling 20, engagement member 22, tether 24, and spokes 30. As discussed above with reference to FIGS. 1-6, 8-11, and 13, tether 24 may include engagement member 22 at fixed end 28 for facilitating attachment with coupling member 36 at the distal end of inner delivery wire 34. For example, FIG. 13 shows that a proximal end of engagement member 22 may have threaded internal bore 56 that is sized and configured for receiving externally threaded coupling member 36. Thus, engagement member 22 may be configured as an internally threaded end screw for receiving coupling member 36 of inner delivery wire 34 in a threaded engagement such that rotation of inner delivery wire 34 in a clockwise or counterclockwise direction facilitates attachment to and detachment from engagement member 22 depending on the direction in which inner delivery wire 34 is rotated. Additional description of a method for attaching and detaching inner delivery wire 34 and engagement member 22 is described in further detail below with reference to FIGS. 14A-D and 15. It is understood that the illustrated engagement between engagement member 22 and coupling member 36 is not meant to be limiting, as the threads may be reversed such that engagement member 22 is externally threaded and coupling member 36 is internally threaded. Furthermore, other suitable techniques may be used to engage and disengage coupling member 36 from engagement member 22 in response to manipulation of inner delivery wire 34 while providing the ability to transmit torque, such as a press fit, snap fit, twist-fit, and the like. In one embodiment, medical device 48 may be able to be recaptured prior to coupling member 36 being withdrawn proximally of threaded proximal coupling 20. For example, inner delivery wire 34 may include a marking or etching on the proximal end of inner delivery wire 34 such that the point of locking the device can be determined without the use of other imaging modalities through the visualization of such markings in relation to outer delivery wire 38.

In this regard, prior to spokes 30 being locked and engaged, the device can be recaptured by assuring that outer delivery wire 38 is engaged with threaded proximal coupling 20 and pulling the device into the sheath with the identified delivery wire. Once spokes 30 have been engaged, the device may still be recaptured, but spokes 30 must first be disengaged. Such disengagement can be accomplished with outer delivery wire 38 or other catheter having an internal diameter that is smaller than or equal to the inner diameter of the through lumen provided in proximal end 15 of the device. The catheter or outer delivery wire 38 may be used to disengage spokes 30 and allow spokes 30 to be pushed back into the device. The device may then be recaptured in a manner similar to the manner described above.

Figure 14A:
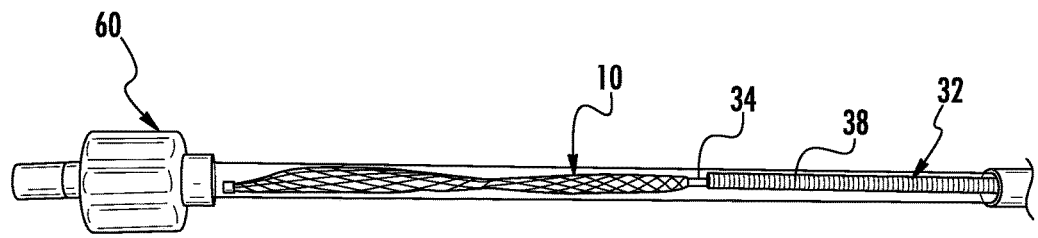
FIG. 14A is a schematic illustration of a medical device engaged with a delivery device and disposed within a delivery catheter according to one embodiment of the present disclosure.

FIG. 14A illustrates an embodiment of a system for delivering a medical device, such as medical device 10, to a target site. In this regard, FIG. 14A shows medical device 10 coupled to delivery device 32 including inner delivery wire 34 and outer delivery wire 38. In particular, medical device 10 is coupled to inner delivery wire 34, and medical device 10, inner delivery wire 34, and outer delivery wire 38 are disposed within delivery catheter 60. Delivery catheter 60 is axially displaceable with respect to medical device 10, as well as inner 34 and outer 38 delivery wires. Medical device 10 is configured to be constrained to a reduced configuration for placement within delivery catheter 60. In one example, medical device 10 may be axially elongated to achieve the reduced diameter. For instance, FIG. 2 illustrates medical device 10 in a relaxed configuration, and medical device 10 may be axially elongated from the relaxed configuration to the reduced configuration for placement within delivery catheter 60. Thus, medical device 10 may be radially constrained to a reduced configuration, which allows medical device 10 to be positioned within a small diameter delivery catheter. As such, medical device 10 is configured to be delivered through small diameter passageways and subsequently expand to its expanded, locked configuration when deployed at the target site, as explained in further detail with respect to FIGS. 14B-D and 18

Figure 14B:
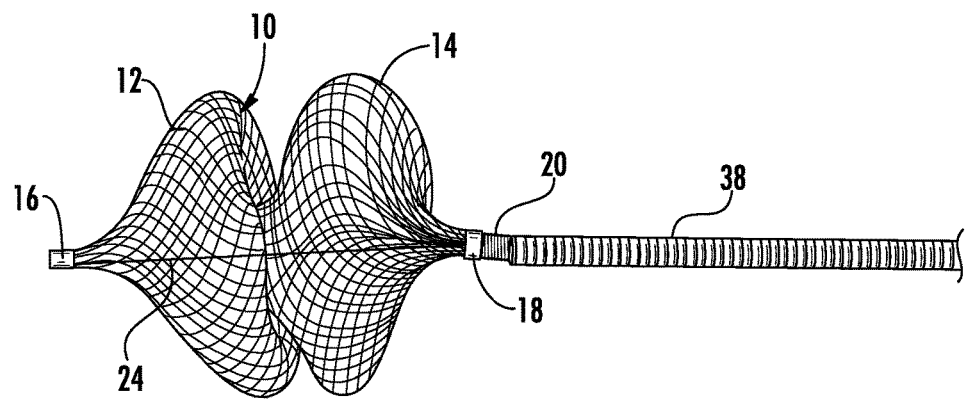
FIG. 14B is a schematic illustration of the medical device of FIG. 14A deployed from the delivery catheter and in engagement with the delivery device.
Figure 14C:
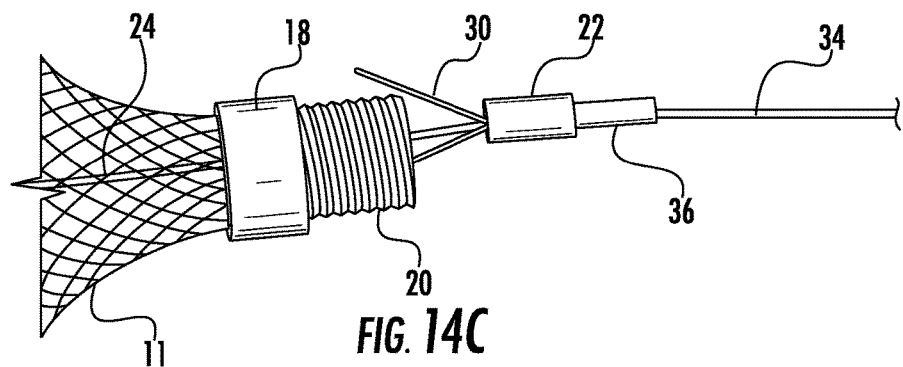
FIG. 14C is an enlarged schematic illustration of the medical device of FIG. 14A in engagement with the delivery device and the delivery catheter withdrawn.
Figure 14D:
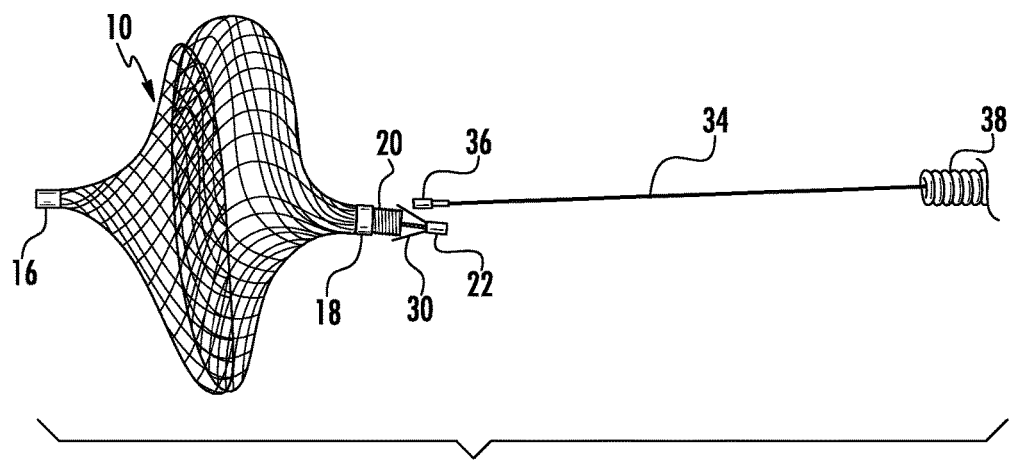
FIG. 14D is a schematic illustration of the medical device of FIG. 14A in an expanded configuration and disengaged from the delivery device.

FIGS. 14B-D illustrate one embodiment of a sequence for deploying a medical device at a target site. In this regard, FIG. 14B illustrates medical device 10 in a partially expanded configuration whereby delivery catheter 60 has been withdrawn, and inner delivery wire 34 and outer delivery wire 38 are displaced relative to one another. For instance, inner delivery wire 34 (see e.g., FIGS. 1, 2, 4, 6, 9, and 13), while coupled to engagement member 22 (see e.g., FIGS. 1-6, 8-10, and 13), may be withdrawn in a proximal direction, while outer delivery wire 38 is held stationary. Thus, engagement member 22 and spokes 30 (see e.g., FIGS. 1-6, 8-10, and 13) will be withdrawn towards proximal end 15. In another embodiment, inner delivery wire 34 may be held stationary to maintain distal placement while outer delivery wire 38 is advanced distally to engage coupling of engagement member 22 and spokes 30 with proximal end 15. FIG. 14B also shows medical device 10 in a partially expanded configuration whereby proximal disk 14 and distal disk 12 are partially expanded due to the tendency of medical device 10 to be biased towards its relaxed configuration when unconstrained. In addition, FIG. 14C shows that withdrawing inner delivery wire 34 through clamp 18 and threaded proximal coupling 20, also withdraws engagement member 22 and spokes 30 through clamp 18 and threaded proximal coupling 20, thereby releasing spokes 30 such that spokes 30 may expand and engage threaded proximal coupling 20. Once each spoke 30 has been released and expanded to engage threaded proximal coupling 20, coupling member 36 of inner delivery wire 34 may be detached from engagement member 22, as shown in FIG. 14D. After the desired placement is determined, outer delivery wire 38 may also be disengaged from threaded proximal coupling 20. According to one embodiment, inner delivery wire 34 and outer delivery wire 38 are similar to the ITV-FX delivery system manufactured by AGA Medical Corporation. For example, inner delivery wire 34 may a flexible core wire (e.g., a Nitinol material), while outer delivery wire 38 may be a coiled wire (e.g., a stainless steel material).

Figure 15:
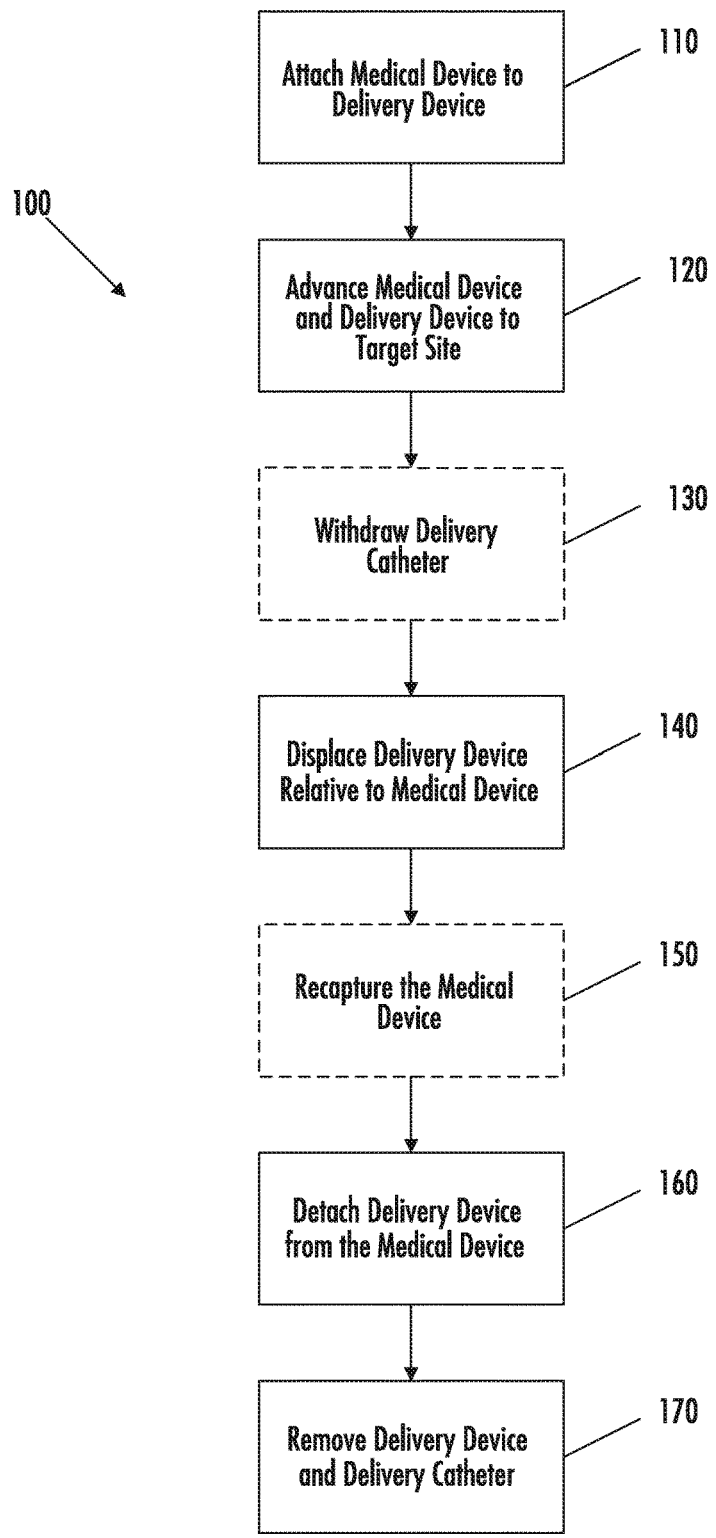
FIG. 15 is a flowchart illustrating a method of delivering a medical device according to an embodiment of the present disclosure.

In FIG. 15, a method for delivering a medical device to a target site, such as medical device 10 described above, is summarized (Block 100). A delivery device configured as described above in connection with one or more of FIGS. 1-2, 4, 6, 9, and 14A-14D may be used to deliver the medical device. For example, the delivery device may include an inner delivery wire and an outer delivery wire. The inner delivery wire may include a coupling member configured to attach to and detach from an end of the medical device.

The medical device may be attached to the delivery device, such as via attachment of the coupling member of the inner delivery wire to the medical device (Block 110). An example of attachment between a medical device and a delivery device is illustrated and described with reference to FIGS. 1, 2, 9, and 13. Attachment of the medical device may occur, in some cases, at a facility at which the delivery device is manufactured, such that an operator of the delivery device receives the delivery device and the medical device already attached. Alternatively, the medical device may be attached to the delivery device at the time of use or implantation or at a separate location from where the delivery device is manufactured. The delivery device and the medical device may then be advanced through a delivery catheter to the target site while the medical device is in a reduced configuration (Block 120). An example of a delivery device and medical device in a reduced configuration for advancement through a delivery catheter is illustrated and described with reference to FIG. 14A. The delivery catheter may then be withdrawn to partially deploy the medical device (Block 130) (see e.g., FIGS. 14A-B). An example of a partially deployed medical device and withdraw of a delivery catheter is illustrated and described with reference to FIG. 14B. The delivery device may then be displaced relative to the medical device to fully expand the medical device to an expanded configuration (Block 140). For example, the delivery device and medical device may be displaced such that the medical device is compressed towards the expanded configuration as illustrated and described with reference to FIGS. 1, 3, 5, and 8. In the expanded configuration, the engagement member engages the proximal end of the medical device such that the medical device is locked in the expanded configuration as illustrated and described with reference to FIG. 13.

The medical device may then be detached from the delivery device at (Block 160). An example of detachment of a medical device and a delivery device is illustrated and described above with reference to FIGS. 13 and 14A-14D. The delivery device and the delivery catheter may be withdrawn from the target site (Block 170). In some cases, at Block 150, the medical device may be recaptured by engaging an outer delivery wire of the delivery device to the medical device, such as in cases where the medical device is to be repositioned (e.g., when the medical device is deployed in an incorrect location or could be more favorably positioned). In this regard, the medical device may be capable of being captured through use of the outer delivery wire or other hollow shaft of similar internal diameter as the threaded proximal coupling to disengage the spokes and elongate the device into the delivery configuration. As noted above, the inner delivery wire may include a marking or etching at the proximal end of the outer delivery wire such that the point of locking the device or engaging the spokes can be determined so as to provide a visual indication of whether disengagement of the spokes is needed in the recapturing of the device.

The method depicted in FIG. 15 and described above represents only one possible method for delivering a medical device for treating a target site. It is understood that the illustrated steps in FIG. 15 may be performed in any desired order and should not be limited to the illustrated embodiments. In some embodiments, certain steps described above may be modified, omitted, or further amplified. Furthermore, in some embodiments, additional optional steps may be included, some examples of which are shown in dashed lines in FIG. 15. Modifications, additions, omission, or amplifications to the steps above may be performed in any order and in any combination. The particular methods of manufacturing and delivery will depend on the desired configuration of the medical device, the patient's anatomy, the condition and location of the target site, the preferences of the practitioner, and/or other considerations.

The medical device may be configured to occlude a target site following deployment. In instances where the medical device comprises a braided fabric formed from a plurality of braided strands as discussed above with reference to FIGS. 1 and 2, over time thrombi will tend to collect on the surface of the strands when the medical device is deployed in a patient. By having a greater strand density and smaller flow passages between strands as afforded by the braided construction of the medical device, the total surface area of the strands and flow resistance will be increased, increasing the thrombotic activity of the device and permitting it to relatively rapidly occlude the target site in which it is deployed. When locked in the expanded configuration, the medical device is able to achieve an increased radial force and pull-out force, thereby reducing incidences of migration at the target site. In addition, the ability to lock the medical device in an expanded configuration facilitates smaller delivery catheter sizing since the medical device can be formed of softer materials and smaller diameter braided strands thereby being capable of achieving smaller reduced diameters for delivery to the target site. Moreover, locking the medical device in the expanded configuration can be used to provide compression at the target site, such as where the medical device is compressed onto opposite sides of a thin membrane at the target site, which provides for adequate pressure without damaging or otherwise distorting the underlying tissue.

In one use of the embodiments discussed above, the medical device may be used to treat an aortic valve. In this regard, the medical device may provide adequate radial force to resist migration and close or otherwise occlude the aortic valve to prevent backflow of blood from the heart. In this regard, following LVAD (Left Ventricular Assist Device) implantation, the aortic valve may experience aortic insufficiency due to the valve not fully closing. The medical device may be configured to occlude the aortic valve to prevent blood from leaking through the aortic valve in a reverse direction thereby reducing the incidence of regurgitation. The medical device may also be configured to withstand the pressure induced by the LVAD following deployment at the aortic valve. For example, the medical device may be configured to clamp opposite sides of the valve to secure the valve leaflets therebetween.

Many modifications and other embodiments of the disclosure set forth herein will come to mind to one skilled in the art to which these embodiments pertain having the benefit of the teachings presented in the foregoing descriptions and the associated drawings. Therefore, it is to be understood that the above-described embodiments are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A medical device for treating a target site, the medical device comprising:
    a tubular member formed of a braided fabric comprising a plurality of braided strands extending from a proximal end to a distal end of the tubular member, the tubular member having an expanded configuration and a relaxed configuration, the relaxed configuration comprising a plurality of disk members, the tubular member configured to be constrained from the relaxed configuration to a reduced configuration for delivery to the target site, the tubular member configured to at least partially return from the reduced configuration to the relaxed configuration when unconstrained;
    a tether comprising a first end and a second end, the first end fixed to the proximal end or the distal end of the tubular member; and
    an engagement member coupled to the second end of the tether and disposed at least partially within the tubular member and between the proximal and distal ends of the tubular member in the relaxed configuration, the engagement member configured to engage the proximal or distal end of the tubular member, opposite the first end of the tether, upon displacement of the proximal and distal ends of the tubular member towards one another such that the tubular member is locked in the expanded configuration.

2. The medical device of claim 1, wherein the engagement member comprises at least one spoke.

3. The medical device of claim 2, wherein the at least one spoke comprises a resilient material.

4. The medical device of claim 1, wherein the engagement member comprises a plurality of spokes.

5. The medical device of claim 1, wherein a length of the tether is less than a length between the proximal end and the distal end of the tubular member in the reduced configuration and the relaxed configuration.

6. The medical device of claim 1, further comprising a pair of end clamps, one of the pair of end clamps secured to the proximal end of the tubular member and the other of the pair of end clamps secured to the distal end of the tubular member.

7. The medical device of claim 6, wherein one of the pair of end clamps comprises an opening defined therethrough, and wherein the tether and the engagement member are configured to be axially displaced through the opening.

8. The medical device of claim 6, further comprising a threaded proximal coupling coupled to one of the pair of end clamps and configured to removably attach to a delivery device.

9. The medical device of claim 1, wherein the engagement member is configured to removably attach to a delivery device.

10. The medical device of claim 1, wherein the tether comprises a single strand of material.

11. The medical device of claim 1, wherein the tether comprises a shape-memory metal material.

12. The medical device of claim 1, wherein the engagement member comprises at least one spoke extending radially outward from the tether and in a proximal-to-distal direction.

13. The medical device of claim 1, further comprising a holder disposed on the tether and between the first end and the second end thereof, wherein the holder is configured to house the engagement member therein while the tubular member is in the reduced configuration and the relaxed configuration, and wherein the engagement member is configured to be displaced from the holder to engage the proximal end or the distal end of the tubular member, opposite the first end of the tether, in the expanded configuration.

14. The medical device of claim 1, wherein the tubular member is configured to be compressed from the relaxed configuration to the expanded configuration.

15. The medical device of claim 1, wherein a maximum outer diameter of at least one disk member is larger in the expanded configuration than the relaxed configuration.

16. The medical device of claim 1, wherein the engagement member is configured to be displaced outside of the tubular member in the expanded configuration.

17. The medical device of claim 16, wherein the engagement member is positioned proximally of the proximal end of the tubular member in the expanded configuration.

18. A medical device for treating a target site, the medical device comprising:
  a tubular member formed of a braided fabric comprising a plurality of braided strands extending from a proximal end to a distal end of the tubular member, the tubular member having a preset configuration in a relaxed state comprising a plurality of disk members and an expanded configuration, the tubular member configured to be constrained to a reduced configuration for delivery to the target site;
  a tether comprising a first fixed end and a second free end, the first fixed end coupled to the proximal or distal end of the tubular member;
  an engagement member coupled to the second free end of the tether and configured to engage the proximal or distal end of the tubular member, opposite the first fixed end of the tether, such that the tubular member is locked in the expanded configuration; and
  a holder disposed on the tether and between the first fixed end and the second free end thereof, wherein the holder is configured to house the engagement member therein when the tubular member is in the reduced configuration, and wherein the engagement member is configured to be displaced from the holder to engage the proximal end or the distal end of the tubular member, opposite the first fixed end of the tether, in the expanded configuration.

19. The medical device of claim 18, wherein the first fixed end of the tether is fixedly attached to the distal end of the tubular member and the engagement member is configured to engage the proximal end of the tubular member in the expanded configuration.

20. The medical device of claim 18, wherein the tubular member is configured to be compressed from the preset configuration to the expanded configuration.

21. The medical device of claim 18, wherein the engagement member comprises at least one spoke extending radially outward from the tether and in a proximal-to-distal direction.

22. The medical device of claim 18, wherein the second free end of the tether is disposed at least partially within the tubular member and between the proximal and distal ends of the tubular member in the reduced configuration.

23. The medical device of claim 18, wherein the engagement member comprises at least one spoke, and wherein the holder is configured to restrain the spoke from expanding.

* * * * *